US009308333B2

(12) United States Patent
Minocchieri et al.

(10) Patent No.: US 9,308,333 B2
(45) Date of Patent: Apr. 12, 2016

(54) INHALATION THERAPY DEVICE FOR USE IN PREMATURE BABIES AND INFANTS

(71) Applicant: PARI Pharma GmbH, Starnberg (DE)

(72) Inventors: Stefan Minocchieri, Rafz (CH); Thomas Gallem, Munich (DE); Martina Vogelmann, Wielenbach (DE)

(73) Assignee: PARI Pharma GmbH, Starnberg (DE)

(*) Notice: Subject to any disclaimer, the term of this patent is extended or adjusted under 35 U.S.C. 154(b) by 0 days.

(21) Appl. No.: 14/635,362

(22) Filed: Mar. 2, 2015

(65) Prior Publication Data

US 2015/0174344 A1 Jun. 25, 2015

Related U.S. Application Data

(63) Continuation of application No. 11/704,819, filed on Feb. 9, 2007, now Pat. No. 8,985,100.

(30) Foreign Application Priority Data

Feb. 10, 2006 (DE) ........................ 10 2006 006 183

(51) Int. Cl.
*A61M 11/02* (2006.01)
*A61M 11/00* (2006.01)
(Continued)

(52) U.S. Cl.
CPC ............ *A61M 11/02* (2013.01); *A61M 11/001* (2014.02); *A61M 11/005* (2013.01); *A61M 16/00* (2013.01); *A61M 16/0003* (2014.02); *A61M 16/0006* (2014.02); *A61M 16/0054* (2013.01); *A61M 16/0069* (2014.02); *A61M 16/04* (2013.01); *A61M 16/0816* (2013.01);
(Continued)

(58) Field of Classification Search
CPC ................ A61M 11/00–11/005; A61M 11/02; A61M 16/18; A61M 16/10; A61M 16/104; A61M 16/14; A61M 16/147; A61M 16/16; A61M 15/0085; A61M 15/009; A61M 15/08; A61M 15/00; A61M 2016/10; A61M 2016/1005
See application file for complete search history.

(56) References Cited

U.S. PATENT DOCUMENTS 5,078,131 A 1/1992 Foley
5,261,397 A 11/1993 Grunstein
(Continued)

FOREIGN PATENT DOCUMENTS

WO WO 2005/048982 6/2005
WO WO 2005/102431 11/2005

OTHER PUBLICATIONS

Search Report dated Nov. 9, 2015 from European Application No. 15186226.5.

*Primary Examiner* — Rachel Young
(74) *Attorney, Agent, or Firm* — Wolf, Greenfield & Sacks, P.C.

(57) ABSTRACT

For use in premature babies and infants, in particular for administering surfactant to the lungs, the inhalation therapy device described herein comprises an aerosol generating device 1, a respiratory air flow generating means 3 and a nebulizing chamber 5 into which the generated liquid droplets 2 and the respiratory air flow 4 are supplied. The nebulizing chamber 5 comprises a tapering area 52 which ends in a tubular intubation means 6. The intubation means 6 is designed such that the intubation end **6*b*** can be positioned in such a manner that the liquid droplet/respiratory air mixture conveyed via the intubation means is released behind those areas of the respiratory tract that filter out to a great extent the liquid droplets from the mixture.

29 Claims, 6 Drawing Sheets

12: reservoir

14: aerosol generation controller

(51) Int. Cl.

| | |
|---|---|
| ***A61M 16/00*** | (2006.01) |
| ***A61M 16/04*** | (2006.01) |
| ***A61M 16/10*** | (2006.01) |
| ***A61M 16/14*** | (2006.01) |
| ***A61M 16/16*** | (2006.01) |
| ***A61M 16/08*** | (2006.01) |

(52) U.S. Cl.

CPC .......... *A61M 16/108* (2014.02); *A61M 16/109* (2014.02); *A61M 16/1085* (2014.02); *A61M 16/142* (2014.02); *A61M 16/161* (2014.02); *A61M 16/16* (2013.01); *A61M 2202/0488* (2013.01); *A61M 2205/3327* (2013.01); *A61M 2205/3368* (2013.01); *A61M 2206/11* (2013.01); *A61M 2240/00* (2013.01)

(56) References Cited

U.S. PATENT DOCUMENTS

| | | | | |
|---|---|---|---|---|
| 5,277,175 | A | 1/1994 | Riggs et al. | |
| 5,443,059 | A | 8/1995 | Koch et al. | |
| 5,483,953 | A | 1/1996 | Cooper | |
| 5,551,416 | A | 9/1996 | Stimpson et al. | |
| 6,014,972 | A | 1/2000 | Sladek | |
| 6,595,203 | B1 | 7/2003 | Bird | |
| 6,729,334 | B1 | 5/2004 | Baran | |
| 6,748,944 | B1 | 6/2004 | DellaVecchia et al. | |
| 7,854,227 | B2 | 12/2010 | Djupesland | |
| 2003/0000520 | A1 | 1/2003 | Ivri et al. | |
| 2003/0015193 | A1 | 1/2003 | Grychowski et al. | |
| 2004/0134494 | A1 | 7/2004 | Papania et al. | |
| 2004/0163646 | A1 | 8/2004 | Schuster et al. | |
| 2004/0182386 | A1 | 9/2004 | Meier | |
| 2005/0066968 | A1 | 3/2005 | Shofner et al. | |
| 2005/0087189 | A1 | 4/2005 | Crockford et al. | |
| 2005/0263149 | A1 | 12/2005 | Noymer et al. | |
| 2006/0081255 | A1 * | 4/2006 | Miller et al. | 128/207.14 |
| 2006/0107953 | A1 | 5/2006 | Truschel et al. | |
| 2007/0137648 | A1 | 6/2007 | Addington et al. | |
| 2007/0186927 | A1 | 8/2007 | Djupesland et al. | |

* cited by examiner

12: reservoir

14: aerosol generation controller

12: reservoir

14: aerosol generation controller

1: aerosol generating device

34": respiratory air control apparatus

70: pulsation means

1: aerosol generating device

34: respiratory air control apparatus

70: pulsation means

INHALATION THERAPY DEVICE FOR USE IN PREMATURE BABIES AND INFANTS

CROSS REFERENCE TO RELATED APPLICATIONS

This application is a continuation of U.S. patent application Ser. No. 11/704,819 filed Feb. 9, 2007, which claims the priority benefit of German Application No. 10 2006 006 183.7 filed Feb. 10, 2006, which are hereby incorporated by reference to the maximum extent allowable by law.

The present invention relates to an inhalation therapy device for use in premature babies and infants.

Premature babies of less than 34 weeks gestation suffer from a surfactant deficiency syndrome. Synonyms for this disease are: HMD (Hyaline Membrane Disease), respiratory distress syndrome in premature babies, IRDS (Infant Respiratory Distress Syndrome). Surfactant replacement therapy is already well established and belongs to the standard methods of therapy in neonatology (the branch of medicine concerned with premature babies and newborns). In order to indicate the scale of the field of use of an inhalation therapy device according to the invention, reference is made to the fact that in Switzerland, approximately 550 children are born each year before reaching the $35^{th}$ week of pregnancy, and thus potentially have an immature lung for which surfactant replacement therapy is advisable. In other countries, for example in Germany, ten times as many premature babies can be expected.

Surfactant replacement therapy occurs whilst the premature babies/infants are in so-called incubators, i.e. in an environment with controlled temperature and humidity since the premature babies are not yet able to maintain their own body temperature. The surfactant is directly instilled into the trachea in liquid form via a tube. Intubation itself carries various risks, for example injury to the glottis or the trachea, pneumothorax, etc. Furthermore, mechanical ventilation, which generally accompanies instillation, can lead to additional damage to the lungs. However, many premature babies/infants make sufficient respiratory effort of their own and do not need to be intubated against this background. However, in order to deposit the surfactant in the lungs, intubation is the means of choice for instillation of the surfactant.

Whereas surfactant replacement therapy has been researched intensively and is already being widely used, nebulisation of the surfactant is problematic since the surfactant often has a low surface tension, a viscosity that is unfavourable for nebulisation and a tendency to foam. The physical properties of the surfactant have led to almost no consideration being given to nebulisation and administration of the surfactant in the form of an aerosol. Furthermore, a surfactant is generally very expensive, and thus the high deposition losses often observed during aerosol therapy have led to this manner of administering a surfactant not being researched further.

Against this background, the present invention aims to disclose a way of administering surfactant to premature babies and infants as part of an aerosol therapy.

This aim is achieved with an inhalation therapy device having the following features:

- an aerosol generating device for nebulising a fluid and providing liquid droplets;
- respiratory air flow generating means for generating a respiratory air flow;
- a nebulising chamber,
  - to which the liquid droplets and the respiratory air flow can be supplied such that said liquid droplets and said respiratory air mix, and
  - which comprises an area that tapers in such a manner that an outlet provided for the escape of the liquid droplet/respiratory air mixture is formed, and
- a tubular intubation means,
  - which comprises a first end configured for connection to the outlet of the nebulising chamber, and
  - which comprises a second end that is configured for endotracheal/endopharyngeal intubation in such a manner that in the case of intubation via the mouth, the second end can be positioned behind the vocal folds of a patient, and in the case of intubation via the nose, the second end can be positioned behind the nasal cavity in the pharynx of a patient.

The invention combines three essential aspects for the particular field of use, namely the precise generation of an aerosol particularly suitable for administration to premature babies and infants, the application of a slight (optionally pulsatile) positive pressure to the airways/lungs in accordance with the CPAP/BIPAP principle, and the largely loss-free supply of an aerosol via a tapering nebulising chamber and an intubation tube which is expediently designed for this use, in which the nebulising chamber ends. It must furthermore be taken into consideration that owing to the fact that it is possible to realise overall very small distances and dimensions relating to the nebulising chamber, only a very small dead volume advantageously exists. The aerosol to be administered is thus available very early on at the start of a respiratory cycle and reaches deep into the airways and lungs of the child.

An inhalation therapy device according to the invention is therefore, however, also basically suitable for other uses. It may thereby be expedient to adapt the dimensions, in particular of the intubation tube.

As can be seen from the description below, further aspects can be added in order to improve efficiency and effectiveness. Reference is made in this regard in particular to the heating and humidifying of the respiratory air, to the application of a pressure oscillation to the respiratory air flow, to the heating of the liquid to be nebulised and to the sheath-like flow surrounding the generated liquid droplets.

The invention will be described in more detail in the following by means of embodiments. Reference is thereby made to the figures, in which FIG. 1 shows a first embodiment of an inhalation therapy device according to the invention having the basic components;

FIG. 1*a* shows an enlarged view of a part of the embodiment according to FIG. 1 that is designed in a specific manner;

Figure 1:
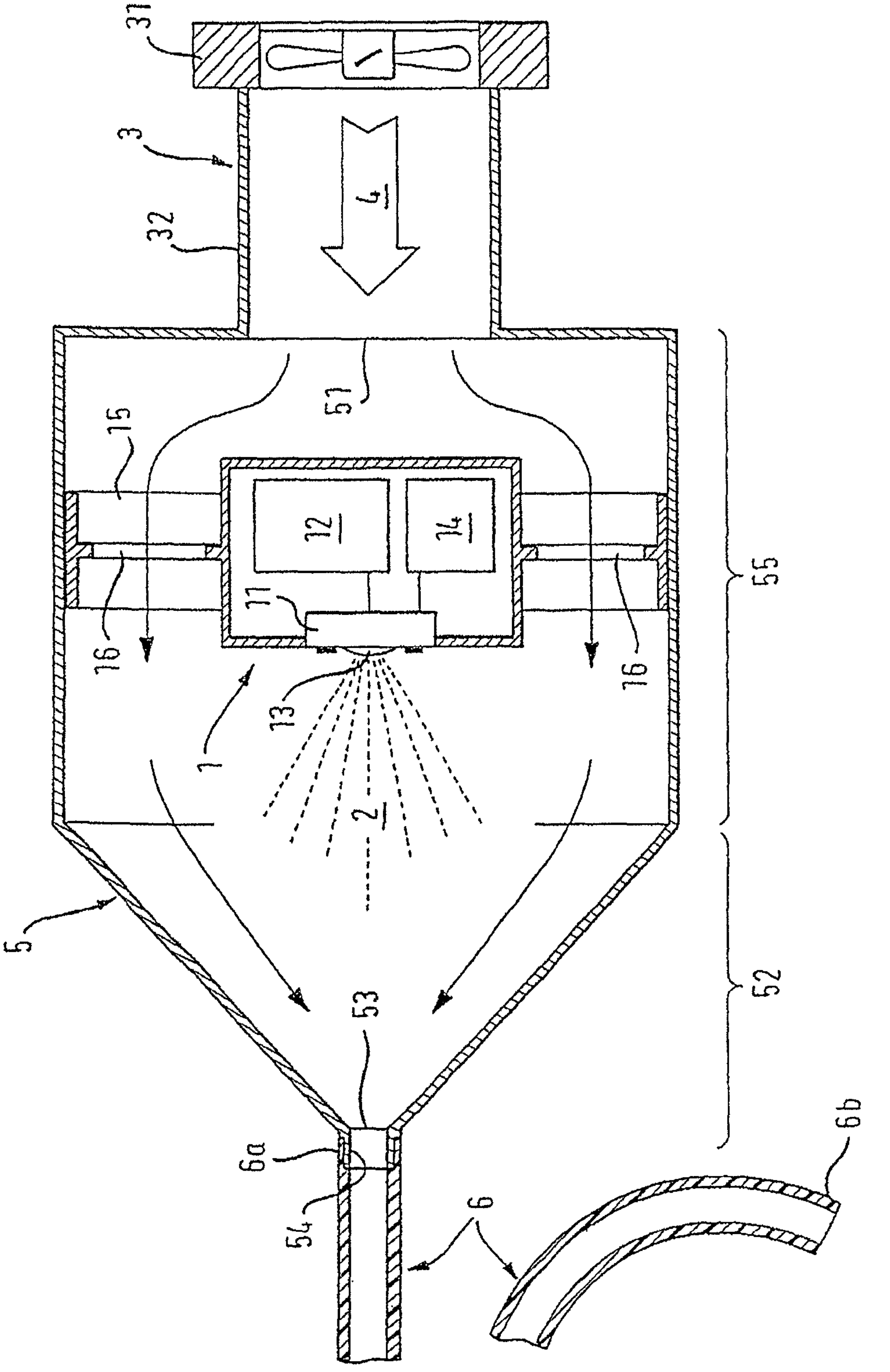

Provided in the embodiment of an inhalation therapy device according to the invention as shown in FIG. 1 is an aerosol generating device 1 for nebulising a fluid and providing liquid droplets 2. In the shown design, the schematically shown aerosol generating device 1 comprises an aerosol generator 11, to which a liquid stored in a reservoir 12 is supplied. In the shown design, the aerosol generator 11 comprises a membrane 13, by means of which the liquid supplied from the reservoir is nebulised such that the aerosol generator 11 releases a defined amount of liquid droplets 2. The aerosol generator 11 is controlled by an aerosol generation controller 14 of the aerosol generating device 1.

In view of the use in premature babies and infants, the size of the liquid droplets (MMD) in an inhalation therapy device according to the invention is between 1.5 and 3 μm. These guidelines can be adhered to with a particularly high degree of accuracy in an aerosol generating device 1 comprising an aerosol generator 11, as already addressed above, with a membrane 13 for generating liquid droplets. An aerosol generating device having a membrane aerosol generator is thus a preferred embodiment of the invention.

The embodiment of an inhalation therapy device according to the invention as shown in FIG. 1 furthermore comprises a means 3 for generating a respiratory air flow 4. For this purpose, the respiratory air flow generating means 3 comprises, for example, a ventilator 31, which generates the respiratory air flow 4 and conveys it into a supply line 32. The pressure and flow of the respiratory air flow 4 can be adapted to the specific therapy situation by appropriately controlling the respiratory air flow generating means 3.

A maximum pressure of 4 to 7 mbar and a tidal volume of approximately 5 ml per kg of body weight are to be used as suitable guidelines for premature babies and infants. Adhering to these guidelines, ventilation of the premature babies/infants is carried out against the background of the ability to breathe independently in accordance with the CPAP principle (Continuous Positive Airway Pressure). The ability of the patient to breathe is always a requirement for the use of CPAP ventilation, however in premature babies and infants, it is advantageously achieved owing to the CPAP positive pressure that the lungs are inflated slightly in advance and the collapse of already ventilated alveoli is prevented. Other methods, such as, for example, according to the BIPAP principle (Biphasic Positive Airway Pressure) can also be used. The pressures that can be applied are dependent on the specific circumstances and can reach, and even exceed, values of 10 mbar (CPAP) and 15 mbar (BIPAP).

The embodiment of an inhalation therapy device according to the invention as shown in FIG. 1 furthermore comprises a nebulising chamber 5, into which both the liquid droplets 2, generated by the aerosol generating device 1, and the respiratory air flow 4, generated by the respiratory air flow generating means 3, are supplied. In the embodiment shown in FIG. 1, this occurs as regards the liquid droplets 2 in that the aerosol generating device 1 is arranged in the nebulising chamber 5 such that liquid droplets 2 are released directly into the nebulising chamber 5. This arrangement of the aerosol generating device 1 also leads to a design of the inhalation therapy system according to the invention in which dead volumes of the nebulising chamber 5 can be reduced to a minimum.

Supply of the respiratory air flow 4 takes place via a respiratory air supply opening 51 of the nebulising chamber 5, at which the supply line 32 of the respiratory air flow generating means 3 is disposed. Supply preferably takes place in such a manner that a turbulent flow forms when the respiratory air 4 enters the nebulising chamber 5. It is ensured in this manner that there is a potential lack of flow through only minimal dead spaces of the nebulising chamber 5 close to the respiratory air supply opening 51, whereby ensuring the best possible supply of oxygen-containing fresh air to the premature/newborn baby. However, the turbulent flow generally ensures that there is flow though the entire or almost the entire nebulising chamber 5. As will be explained below, means are provided in a preferred embodiment of the invention, which convert the turbulent flow into a largely directed flow.

The liquid droplets 2 and the respiratory air 4 mix in the nebulising chamber 5 and, as shown in FIG. 1, reach, owing to the flow determined by the respiratory air 4, a tapering area 52 of the nebulising chamber 5 which ends in an outlet 53. The mixture of liquid droplets and respiratory air, formed by supplying the liquid droplets 2 and the respiratory air 4 into the nebulising chamber 5, can exit the nebulising chamber 5 through the outlet 53 of the nebulising chamber 5.

According to the invention, the embodiment shown in FIG. 1 comprises a tubular intubation means 6, the first end 6*a* of which is configured for connection to the outlet 53 of the nebulising chamber 5. The first end 6*a* of the intubation means 6 can preferably be placed onto a connecting piece 54 of the nebulising chamber 5, which is provided at the outlet 53. As a result of the attachment of the tubular intubation means 6 according to the invention, the liquid droplet/respiratory air mixture escapes from the nebulising chamber 5 via the outlet 53 and into the tubular intubation means 6, flows herethrough and arrives at the second end 6*b* of said tubular intubation means 6.

In order to ensure a largely deposit-free transport of the liquid droplet/respiratory air mixture through the intubation means, a tube having an inner diameter of 2 to 3.5 mm is expediently used. To again minimise deposition losses, the entire length of the tubular intubation means should not exceed 50 cm. Very good results, which could not be expected in view of the passages for the aerosol that seem comparatively small, are surprisingly achieved if these guidelines are adhered to. This is all the more true in the case of a surfactant as the liquid to be nebulised, whose physical properties do not give rise to the anticipation that if certain guidelines are adhered to and suitable nebulisation is carried out, an aerosol administration of a surfactant to premature babies and infants is possible by way of inhalation.

The second end of the intubation means 6 is designed for endotracheal/endopharyngeal intubation, with design being advantageously carried out according to the invention such that in the case of orotracheal intubation via the mouth, the second end can be positioned behind the vocal folds of the patient, and in the case of nasopharyngeal intubation via the nose, the second end can be positioned behind the nasal cavity in the pharynx of the patient. Owing to the position-ability according to the invention of the second end 6*b* of the tubular intubation means 6, it is ensured that the liquid droplet/respiratory air mixture conveyed via the intubation means arrives behind the respective regions of the respiratory tract of the patient which carry out intense filtering. In the case of application via the nose, it is necessary to bridge the nasal area and release the liquid droplet/respiratory air mixture in the pharynx of the patient, whereas in the case of application via the mouth, the liquid droplet/respiratory air mixture is preferably released behind the glottis. As regards the design of the intubation end 6*b* according to the invention, emphasis is consequently on the length of this area since the length of the second end 6*b* of the intubation means 6 determines at which point of the patient's respiratory tract the liquid droplet/respiratory air mixture (of the aerosol) is released. In premature babies and infants, a length of approximately 15 cm is expedient.

Owing to the cooperation of the individual components of the inhalation therapy device according to the invention as shown in FIG. 1, it is achieved that the liquid droplets 2 and the respiratory air flow 4 are brought together in the nebulising chamber 5, mix therein and are conveyed as a liquid droplet/respiratory air mixture, i.e. as an aerosol, via the tapered area 52 of the nebulising chamber into the intubation means 6 to be released from the intubation means behind the regions of the respiratory tract of the patient which carry out intense filtering. The inhalation therapy device according to the invention therefore achieves a particularly effective administration of the nebulised liquid, and thus areas of application open up for the inhalation therapy device according to the invention, which were not accessible with conventional devices owing to a lack of administration accuracy and effectiveness.

It is thus possible, as mentioned above, to administer surfactant to premature babies and infants using an inhalation therapy device according to the invention. Surfactant reduces the surface tension in the alveoli and thus makes breathing easier for the children, which leads to an improved oxygen uptake. The positive effect of treatment with surfactant is frequently described in literature. However, the administration of a surfactant aerosol that can be administered by means of the inhalation therapy device according to the invention is not known. This possibility is created by the invention since the overall concept of the inhalation therapy device according to the invention, which consists of several aspects, leads to the provision of a therapy device which makes it possible to administer a surfactant in this manner.

It must be stated with regard to the embodiment shown in FIG. 1 that the arrangement of the aerosol generating device 1 inside the nebulising chamber 5 is particularly advantageous since an undesirable deposition of the liquid droplets in the nebulising chamber 5 is minimised in this manner. The arrangement also helps to minimise dead space volumes in the nebulising chamber 5. The aerosol generator 11 of the aerosol generating device 1 can furthermore be arranged such that it is aligned in a suitable manner in relation to the tapered area 52 of the nebulising chamber. If the inhalation therapy device according to the invention is designed basically in a rotationally symmetrical manner, as is indicated in FIG. 1, this means that the aerosol generator 11 of the aerosol generating device 1 is located on the axis of rotation in such a manner that the liquid droplets move along the axis of rotation in the direction of the tapering area 52. The device according to the invention can therefore also be operated at any position relative to the axis of rotation. Supply of the respiratory air 4 then also occurs along the axis of rotation, and thus a respiratory air flow that flows around the aerosol generating means is established, which is indicated in FIG. 1 by means of corresponding arrows. In order for the respiratory air 4 to be able to flow around the aerosol generating device 1, a holding means 15 of the aerosol generating device 1 comprises through-holes 16 so that the respiratory air 4 can flow virtually unimpeded around the aerosol generating device 1 in the nebulising chamber 5. However, the through-holes 16 advantageously cause a respiratory air flow that is turbulent following entry through the respiratory air supply opening to be converted into a largely laminar flow, which is favourable for a transport of the inflowing liquid droplets that is unaffected as far as possible by inertia forces. Furthermore, the holding means 15 also has a sufficient number of radially extending support elements so that the holding means 15 fixes the aerosol generating device 1 in the area 55 of the nebulising chamber 5 intended therefor.

Figure 1A:
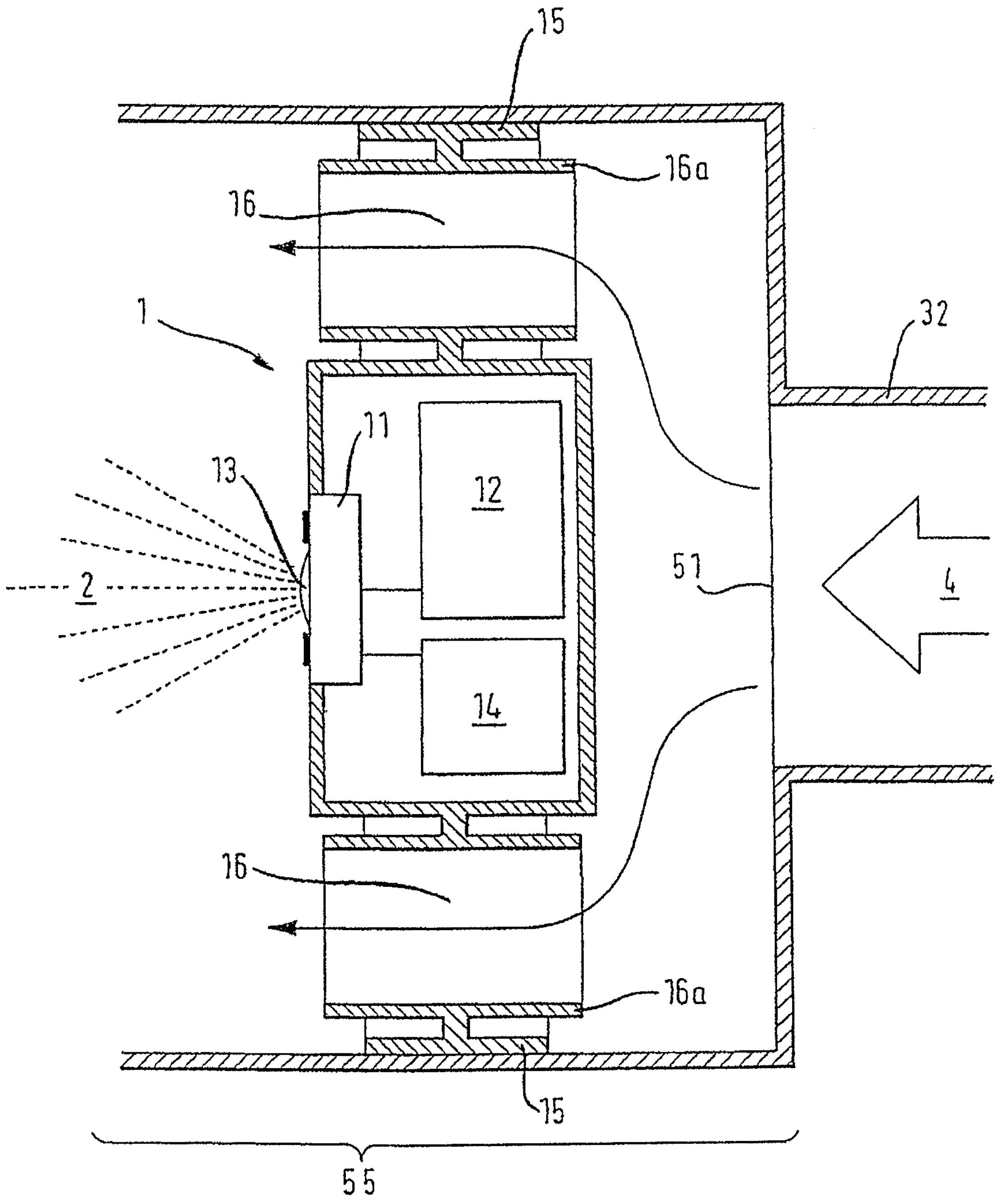

In order to assist conversion of the respiratory air flow into a largely laminar flow, the through-holes 16 can be equipped with respiratory air guides 16*a*, as is shown in FIG. 1*a*. The respiratory air guides are advantageously short, tubular elements 16*a* having, for example, a circular cross-section.

Figure 2:
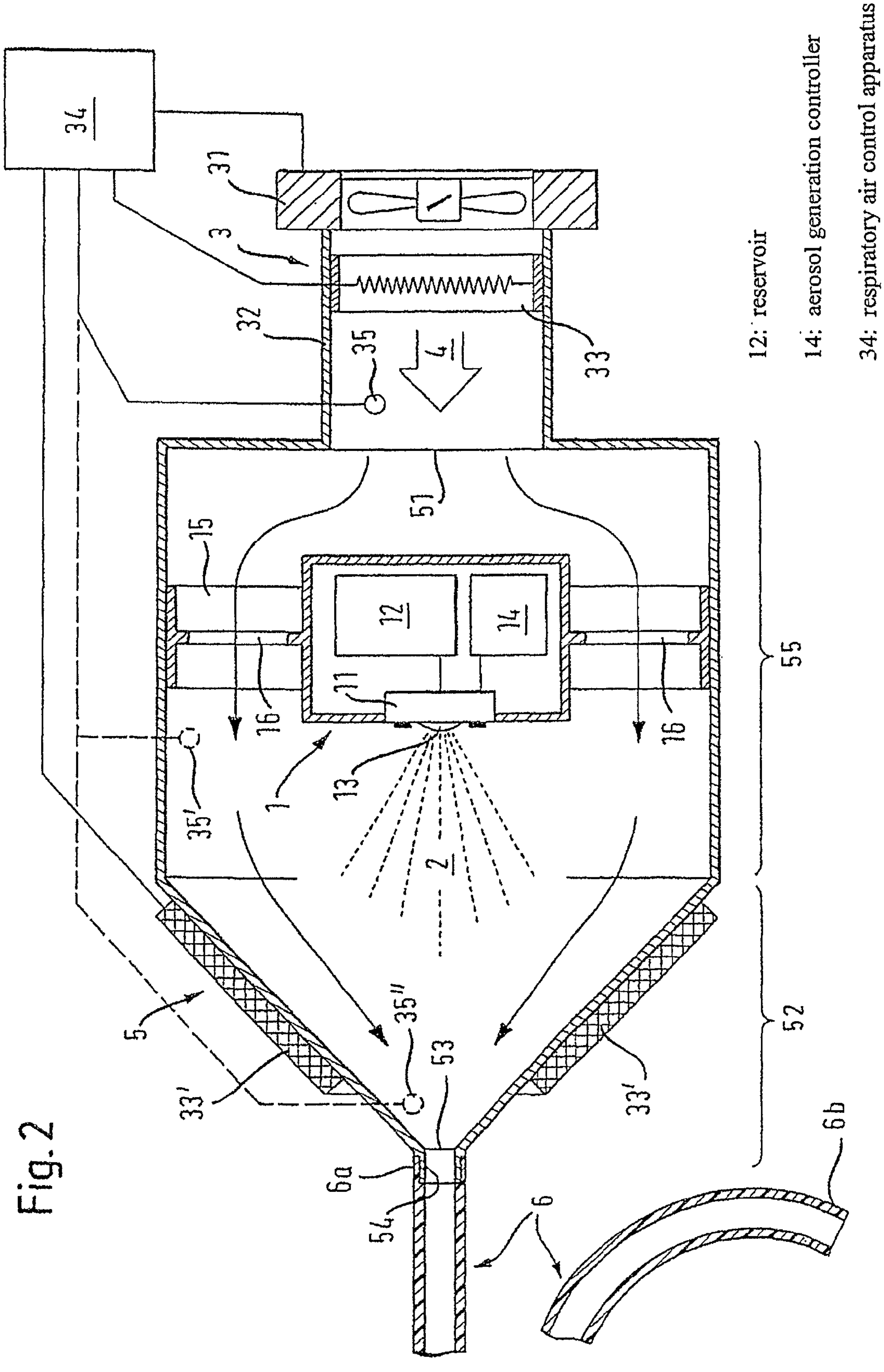
FIG. 2 shows a second embodiment of an inhalation therapy device according to the invention having a respiratory air heating means.

FIG. 2 shows a further embodiment of an inhalation therapy device according to the invention which corresponds to the first embodiment as regards the basic components. Reference is made in this regard to the previous description; FIG. 2 therefore also includes the same reference numbers as used in FIG. 1.

Provided in the second embodiment, as shown in FIG. 2, is a respiratory air heating means 33, which heats the respiratory air 4 supplied by the respiratory air flow generating means 3 into the nebulising chamber 5. A respiratory air control apparatus 34 is provided for control of the respiratory air temperature, which controls the respiratory air heating means 33 based on a measurement signal provided by a temperature sensor 35. The sensor 35 is disposed in the flow of the heated respiratory air 4, for example in the supply line 32 of the respiratory air flow generating means 3. As shown in FIG. 2, the respiratory air sensor 35', 35" can alternatively also be disposed at a suitable position in or on the nebulising chamber 5. In a particularly preferred design, measurement of the temperature is carried out by a sensor 35" in the vicinity of the outlet 53 of the nebulising chamber 5. However, two or more sensors can also be used, for instance to detect the temperature of the respiratory air in the region of the supply line 32 on the one hand and in the region of the outlet 53 on the other, and take it into consideration for the control of the respiratory air heating means 33 by the respiratory air control apparatus 34.

The respiratory air heating means 33 is preferably controlled by the respiratory air control apparatus 34 in such a manner that the respiratory air supplied to the patient via the intubation means is heated to 35° C. to 37° C. The respiratory air control apparatus 34 controls the temperature of the respiratory air so that it is within a narrow range irrespective of the external conditions. The respiratory air control apparatus 34 can thereby be connected with the air conveying means 31 and can control its ventilator in consideration of the measured values supplied to the respiratory air control apparatus 34 by measuring sensors 35, 35' and/or 35".

Finally, a connection between the aerosol generating device 1, more precisely the controller 14 thereof, and the respiratory air control apparatus 34 may be expedient so that the start of nebulisation of the liquid is taken into consideration when controlling the respiratory air heating means 33. The reason for this is that owing to the generation of the liquid droplets 2 in the nebulising chamber 5, cooling of the respiratory air that is present in the nebulising chamber 5 and mixes with the liquid droplets occurs since the liquid droplets are dried by the respiratory air. This drying effect is basically desirable since it is thereby possible to influence the size of the liquid droplets so that the guidelines (see above) can be complied with more accurately. By way of an appropriate control of the heating means 33, it is thus ultimately possible to set the temperature and droplet size (by controlled drying) of the aerosol, in particular if a sensor 35" is placed in the vicinity of the outlet 53 of the nebulising chamber 5. A heating means for the liquid stored in the aerosol generator, which heats the stored liquid, can be provided as a supportive measure. The heating means is preferably controlled by the controller 14.

As an alternative or in addition to the respiratory air heating means 33 shown in FIG. 2, an aerosol heating means 33' can be provided in a further design of the inhalation therapy device according to the invention, which is preferably disposed on the nebulising chamber 5, as is also shown by FIG. 2. The aerosol heating means 33' heats the aerosol by means of IR radiation. The aerosol heating means 33' is also advantageously connected to the respiratory air control apparatus 34 and is, as described above for the heating means 33, included in control. Reference is made to the above description in this respect.

Figure 3:
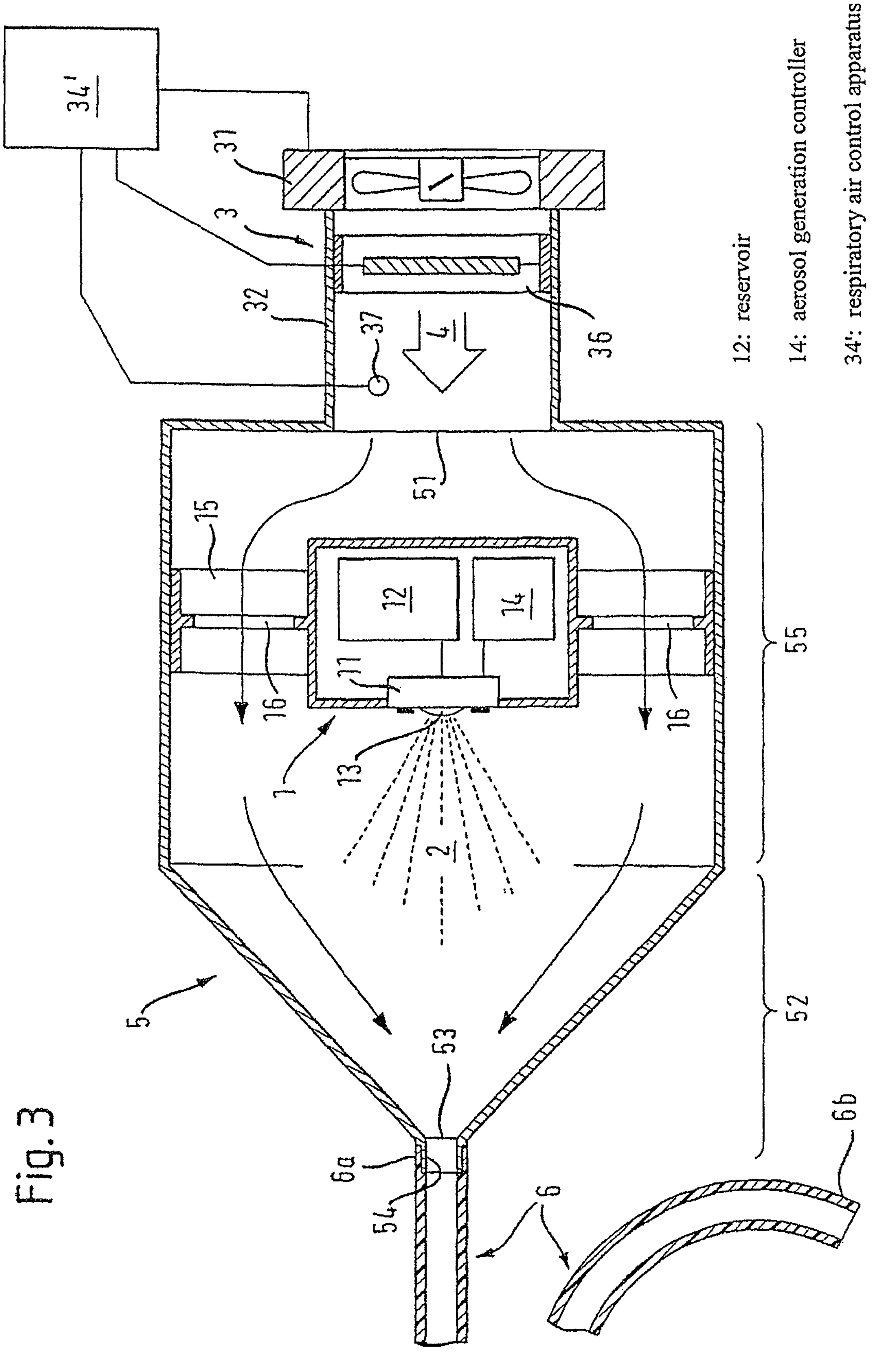
FIG. 3 shows a third embodiment of an inhalation therapy device according to the invention having a respiratory air humidifying means.

FIG. 3 shows a further embodiment of an inhalation therapy device according to the invention. Just like in FIG. 2, the structure of the embodiment according to FIG. 3 essentially corresponds to the structure of the first embodiment. The reference numbers of FIG. 1 are according also present in FIG. 3.

As a modification of the first embodiment, the inhalation therapy device according to the invention in FIG. 3 comprises respiratory air humidifying means 36 disposed relative to the respiratory air flow 4 such that it can humidify the respiratory air supplied by the respiratory air flow generating means 3. The respiratory air humidifying means 36 is controlled by the respiratory air control apparatus 34', which preferably receives a measurement signal from a humidity sensor 37 that is disposed in the humidified respiratory air flow 4 and is connected with the respiratory air control apparatus 34'. The respiratory air control apparatus 34', just like the respiratory air control apparatus 34 described in connection with FIG. 2, is optionally connected with the respiratory air conveying means 31 in order to control the ventilator. Furthermore, the respiratory air control apparatus 34' is preferably connected with the controller 14 of the aerosol generating device 1 so as to activate the humidifying means 36 in the phases in which no aerosol generation, i.e. no release of liquid droplets 2 by the aerosol generating device 1, is taking place. The humidification of respiratory air is particularly advantageous in these phases, whereas respiratory air that is too humid during administration of the medicament, i.e. when the aerosol generator 11 is activated, prevents further drying of the droplets 2 by the supplied respiratory air 4.

Figure 4:
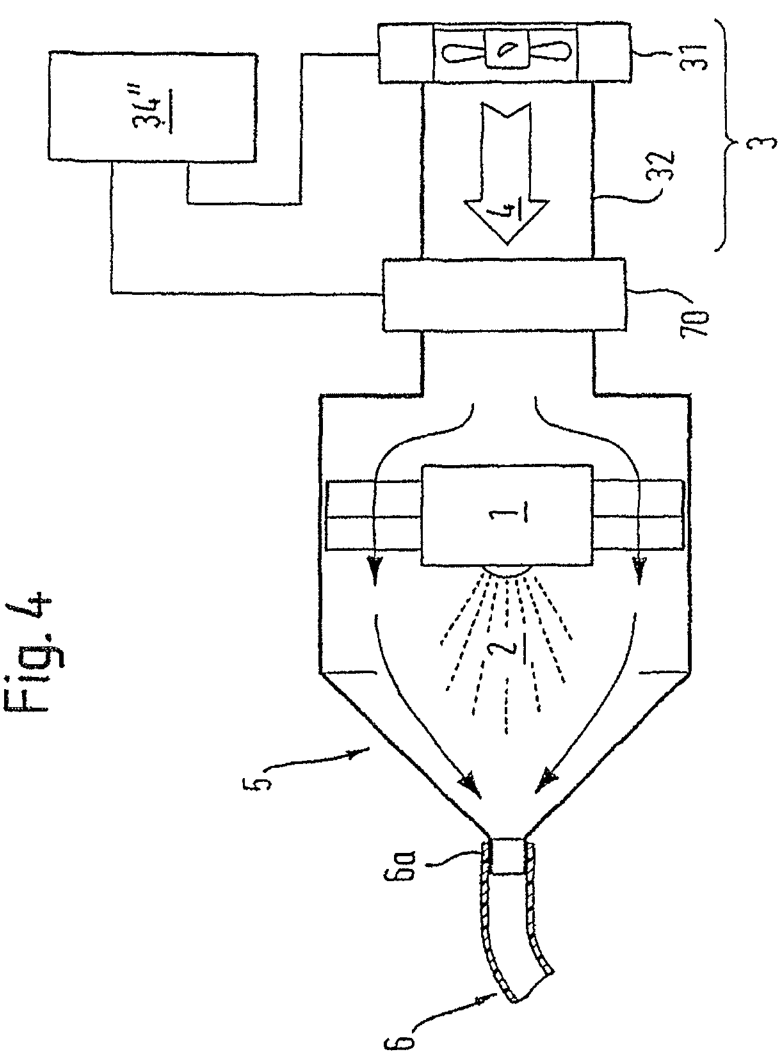
FIG. 4 shows a fourth embodiment of an inhalation therapy device according to the invention having a respiratory air flow pulsation means.

FIG. 4 shows a fourth embodiment of an inhalation therapy device according to the invention, however in a simplified view in order to reduce complexity. Nevertheless, the fourth embodiment also preferably contains the components which have been described in detail above, particularly in connection with the first embodiment. Reference is inasmuch made to the description of the first to third embodiments, without all of the components being shown again in FIG. 4 and being provided with reference numbers.

Prominent in the fourth embodiment is the respiratory air pulsation means 70, shown in FIG. 4, which acts on the respiratory air flow 4 in order to superimpose pressure oscillations on the supply of respiratory air to the nebulising chamber 5. The respiratory air supplied from the nebulising chamber 5 together with the liquid droplets to the premature baby/infant via the intubation means 6 is thus supplied with a superimposed vibration (pressure fluctuations/oscillations) which can lead to the recruiting of additional areas of the lungs. Recruiting in this context means that a region of the lungs not previously participating in gas exchange is activated.

The pulsation means 70, which is schematically shown in FIG. 4, can be realised in various manners, for example by a controllable or automatic valve system or by applying an alternating pressure generated by a piston compressor. The pulsation means 70 is controlled by a respiratory air control apparatus 34", which is preferably also connected with and controls the conveying means 31 of the respiratory air flow generating means 3. The respiratory air control apparatus 34" according to the fourth embodiment can obviously also be connected with the controller 14 of the aerosol generating device 1 in order to perform control of the pulsation means 70 depending on or in consideration of the generation of the aerosol 2.

Figure 5:
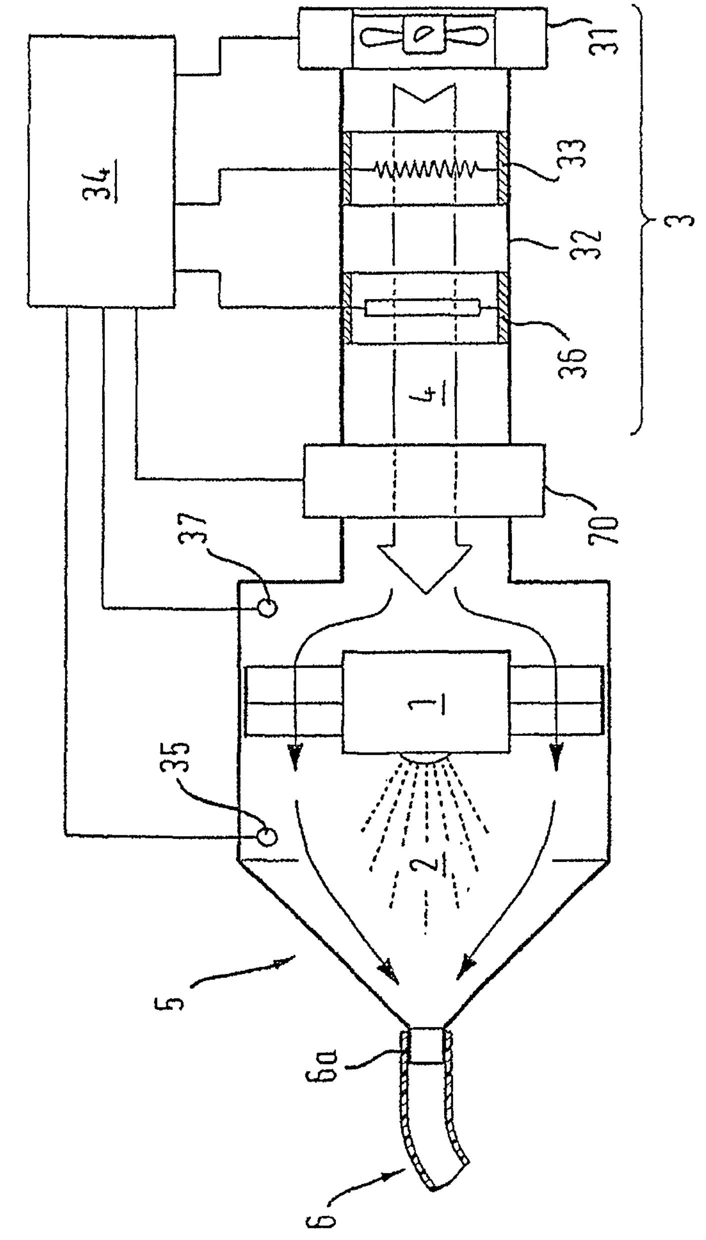
FIG. 5 shows a fifth embodiment of an inhalation therapy device according to the invention having a plurality of additional devices and a control means.

FIG. 5 shows a fifth embodiment of the inhalation therapy device according to the invention, in which the additional components visible in FIGS. 2 to 4 are combined in one device. It is thereby supposed to be expressed by way of an example that the auxiliary devices provided in addition to the basic components can also be used together in different combinations.

In accordance with this aspect, FIG. 5 shows an embodiment in which the respiratory air heating means 33, the respiratory air humidifying means 36 and the pulsation means 70 are all provided in addition to the basic components which were described in detail in connection with FIG. 1 and are not, for this reason, described here in full again and shown in FIG. 5. The respiratory air control apparatus 34 assumes control of the respiratory air heating means 33, the respiratory air humidifying means 36 and the pulsation means 70, and is connected with the means 33, 36 and 70 for this purpose. The respiratory air control apparatus 34 is furthermore preferably connected with the conveying means 31 of the respiratory air flow generating means 3. The respiratory air control apparatus 34 receives measurement signals from the temperature sensor(s) 35, 35', 35" and the humidity sensor 37, which are both schematically shown in FIG. 5. Not shown in FIG. 5 is a connection between the respiratory air control apparatus 34 and the controller 14 present in the aerosol generating device 1 (cf. FIGS. 1 to 3), which is expediently provided in order to perform control of the means 33, 36 and 70 as well as 31 in consideration of aerosol generation by the aerosol generating device 1.

As can be seen from all of the figures and the embodiments shown therein, the inhalation therapy device according to the invention comprises an aerosol generating device 1, a respiratory air flow generating means 3 and a nebulising chamber 5 to which a tubular intubation means 6 is connected. The nebulising chamber 5 not only comprises a tapering area that ends in the intubation means, but rather also allows the mixing of the supplied respiratory air 4 and the liquid droplets 2, which are supplied to the nebulising chamber 5 by the respiratory air flow generating means 3 and the aerosol generating device 1, respectively. In a particularly advantageous design shown in FIGS. 1 to 5, according to which the aerosol generating device 1 is disposed in the nebulising chamber 5, a respiratory air flow 4, which flows around the aerosol generating device 1, is established around the aerosol generating device 1 owing to the arrangement of the respiratory air flow generating means 3. This advantageously leads to the liquid droplets 2 being surrounded by the respiratory air flow in a sheath-like manner, and thus deposition in the nebulising chamber 5 is almost ruled out without a negative effect on the good mixing of the liquid droplets and the respiratory air 4. Owing to the tapering supply of the respiratory air flow with the liquid droplets conveyed therein, optimal supply of the liquid droplet/respiratory air mixture to the intubation means is carried out. Despite the dimensions required for the intubation device, which may possibly seem small, there is almost no deposition of the liquid droplets, and thus the nebulised fluid, in particular a nebulised surfactant, can be administered almost entirely to the lungs of a premature baby/infant. The design of the intubation tube also contributes to this to a considerable extent, the end of which that is intended for intubation being designed such that release does not occur until after the areas of the respiratory tract that carry out filtering (see above).

In the above description of the invention, reference was made in particular to the administration of a surfactant. However, it is also apparent from the description of the invention that an inhalation therapy system according to the invention is basically suitable for the inhalational administration of medicaments of any type, in order to provide newborn or premature babies with a topical or systemic medicinal therapy using the inhalation therapy system according to the invention, characterised in that bodily functions and/or an unnatural or abnormal state are transformed back into a normal state and suffering is alleviated or cured.

The medicinal therapy is characterised in that using the inhalation therapy system according to the invention, medicaments of any type and class from animal, bacterial, human or synthetic material can be administered particularly advantageously by way of inhalation, such as, for example,

- lung surfactant (such as, for instance, Surfaxin),
- anti-inflammatory agents such as steroids (Ciclesonide, Fluticasone),
- non-steroidal anti-inflammatory agents (such as, for instance, Ibuprofen, Celecoxib),
- betamimetic agents (such as, for instance, Indacaterol, Formoterol, Levalbuterol),
- anti-cholinergic agents (such as, for instance, Thiotropium, Glycopyrrolate, Ipratropium),
- phosphodiesterase inhibitors (such as, for instance, Sildenafil, Vardenafil, Tadalafil),
- endothelin antagonists (such as, for example, Bosentan, Sixtasentan, Tezosentan),
- leukotriene antagonists (such as, for instance, Montelukast),
- diuretics (such as, for instance, Furosemide, Amiloride),
- immunomodulators (such as, for instance, Cyclosporin, Mofetil, Sirolimus, Tacrolimus),
- antihypertensive agents (such as, for example, Statins, Sartans, calcium and angiotension antagonists),
- mucolytics (such as, for instance, Dornase alpha, Bromhexine, Ambroxol, Acetylcysteine),
- antibiotics of a variety of classes such as chinolons, macrolides, cephalosporins, aminogylcosides, ketolides, peptides and proteins,
- interferons,
- immunoglobulins,
- prostins,
- antimycotics,
- antiviral agents,
- heparin and heparinoids,
- cytostatics,
- endogenous substances which, owing to a gene defect such as, for instance, mucoviscidosis, or to illness, are not available in sufficient amounts in the body, such as, for instance, alpha-antitrypsin, interferons, insulin, etc.

These substances can be used in the form of acids or alkalis as pharmaceutically common salts or complexes, prodrugs or their optically active antipodes, stereoisomers, enantiomers alone or in combinations.

Particularly suitable medicament formulations are characterised in that they can be nebulised as aqueous preparations in volumes of 0.3 to 10 ml and particularly preferred in volumes of 0.5 to 5 ml, and, with the inhalation therapy system according to the invention, an aerosol having a mass median diameter (MMD) of less than 5 μm, particularly preferred of less than 3.5 μm, and a narrowband particle distribution can be generated, which is distinguished by a geometric standard deviation of less than 2 and particularly preferred of less than 1.6, whereby an in vitro lung dose of >20% and particularly preferred of >25% is achieved in a cast model, which is more than those of conventional inhalation therapy systems with jet nozzle nebulisers.

The inhalational medicament therapy using the innovative inhalation therapy system is characterised in that respiratory clinical symptoms, such as infantile pulmonary diseases, pulmonary distress symptoms, asthma, obstructive bronchitis, bacterial and non-bacterial inflammations, coughs, pulmonary hypertension, parenchymal diseases, genetic defects such as, for example, mucoviscidosis, infantile diabetes, etc., can preferably be treated therewith.

From another perspective, the inhalation therapy system according to the invention can be deemed suitable for the improved inhalational administration of medicaments using an innovative nebuliser concept, which is adapted, in particular, to the requirements of the treatment of premature babies and also normal infants.

In order to achieve a particularly high efficiency, the administration of medicaments can take place using different administration strategies. Since the administration strategy suitable for a particular case depends on various limiting conditions, e.g. on the medicament or medicament combination to be administered, on the structural details of the inhalation therapy system, on the patient group to be treated, etc., a representative example will be explained in the following, which portrays in more detail a field that can be influenced by an administration strategy. Against the background of experimental results showing that if an output rate of the aerosol generator is too high, efficiency is lower than in the case of a reduced output rate, an administration strategy which takes these results into account is suitable. Reduction or adjustment of the output rate of the aerosol generator is essential for the administration strategy explained here as an example, as a result of which the administration strategy leads to increased efficiency. The reduction/adjustment of the output rate can be achieved in a particularly flexible manner by alternately switching on/off the aerosol generator since the output rate can be determined (set) in wide ranges by adjusting/modifying the on/off switching phases.

In order not to compromise the effectiveness of the therapy or to cause a delayed onset thereof, a phase with an increased output rate can precede the phase with a reduced output rate in a specific design of the administration therapy. It is thereby accepted that the efficiency during this preceding phase is lower and a greater amount of medicament must be used than is the case with an optimised output rate. However, it can be achieved by means of the intentionally increased output rate having lower efficiency that the desired effect of the medicament commences at a desired earlier point in time than could be achieved in the case of administration with a reduced output rate from the outset. A reduced output rate can be used with an optimising effect as regards the utilisation of the active substance (=efficiency of administration, minimised loss of active substance in the system). It is obvious that an effective therapy can be combined very flexibly with high efficiency and effectiveness by means of suitable administration strategies.

This aspect shall be explained again in an exemplary manner using the example of the aforementioned surfactant. If, in a first phase of the administration strategy, the surfactant is administered to the premature baby at a high output rate using the inhalation therapy system according to the invention, the stabilising effect of the surfactant on the lungs and an improvement in lung function will be rapidly achieved. Once the lung function of the premature baby has stabilised, the output rate can be reduced in a second phase of the administration strategy with the aim of now optimising use of the surfactant in respect of efficiency, whereby achieving improved utilisation of the valuable active substance, which does not only have to be the aforementioned surfactant.

It is very obvious that a membrane nebuliser is exceptionally suitable as an aerosol generator for implementing the administration strategy explained above. The reason for this is that a membrane nebuliser can be switched on and off in a particularly suitable manner by way of the activation signal to the piezo-oscillator that causes the membrane to oscillate. The pulsed operation, in which aerosol generating phases alternate with resting phases, can be realised very precisely and without any problems. Optimisation for each expedient/required administration strategy can be realised and optimised in this manner.

The invention claimed is:

1. Inhalation therapy device comprising:

an aerosol generating device having a membrane for nebulising a fluid and providing liquid droplets; and a nebulising chamber having a respiratory air supply inlet, the air supply inlet having a center line and being configured to receive a flow of respiratory air from a ventilator, and a connecting piece configured for direct connection to a patient line at an outlet of the nebulising chamber, wherein the liquid droplets and the respiratory air are supplied to and mix in the nebulizing chamber to form a liquid droplet/respiratory air mixture that flows through the outlet, wherein the aerosol generating device is fixed substantially on a center line of the outlet of the nebulising chamber, and wherein the air supply inlet is disposed to direct the flow of respiratory air onto a rear side of the aerosol generating device.

2. Inhalation therapy device according to claim 1, wherein a center line of the air supply inlet is aligned substantially to the center line of the outlet of nebulising chamber.

3. Inhalation therapy device according to claim 1, wherein a respiratory air humidifying device is provided for humidifying the respiratory air.

4. Inhalation therapy device according to claim 3, wherein at least one humidity sensor is provided for supplying a humidity measurement signal.

5. Inhalation therapy device according to claim 3, wherein the respiratory air is humidified in phases in which no liquid droplets are generated.

6. Inhalation therapy device according to claim 1, wherein a respiratory air pulsation device is provided to generate pressure oscillations in the respiratory air.

7. Inhalation therapy device according to claim 1, further comprising an aerosol generation controller for controlling said aerosol generator.

8. Inhalation therapy device according to claim 7, wherein a respiratory air control apparatus is connected with the aerosol generation controller of the aerosol generating device.

9. Inhalation therapy device according to claim 8, wherein the respiratory air control apparatus controls the aerosol generating device.

10. Inhalation therapy device according to claim 1, wherein the aerosol generating device comprises a reservoir for storing the liquid to be nebulised.

11. Inhalation therapy device according to claim 1, wherein the nebulizing chamber has a tapered area, the outlet being disposed at the end of the tapered area.

12. Inhalation therapy device according to claim 1, wherein the aerosol generator is fixed in the nebulising chamber by a holding device comprising a plurality of radially extending support elements for fixing the aerosol generating device.

13. Inhalation therapy device according to claim 12, wherein the holding device comprises a plurality of separated through-holes for the respiratory air supplied to said nebulising chamber.

14. Inhalation therapy device according to claim 1, further comprising:

a tubular intubation device, which comprises a first end configured for connection to the connecting piece of the outlet of the nebulising chamber, and which comprises a second end that is configured for endotracheal or endopharyngeal intubation.

15. Inhalation therapy device according to claim 14, wherein the entire length of the tubular intubation device is not more than 50 cm.

16. Inhalation therapy device according to claim 1, wherein no additional air stream is introduced downstream of the nebulising chamber in a direction to the patient.

17. Inhalation therapy device according to claim 1, wherein the aerosol generating device, the outlet of the nebulising chamber and the respiratory air supply inlet of the nebulising chamber for supply of the respiratory air flow are aligned substantially along one axis and wherein the liquid droplets are provided only in a direction of the respiratory air flow.

18. Inhalation therapy device according to claim 1, wherein the nebulising chamber has a rotationally symmetrical configuration with an axis of rotation, wherein the respiratory air supply inlet is located on the axis of rotation, and wherein the aerosol generating device is fixed in the nebulising chamber on the axis of rotation.

19. Inhalation therapy device according to claim 1, wherein the membrane is positioned substantially on the center line of the outlet of the nebulising chamber.

20. Use of an inhalation therapy system according to claim 1 for the administration of anti-inflammatory agents such as steroids (Ciclesonide, Fluticasone), or non-steroidal anti-inflammatory agents (such as, for instance, Ibuprofen, Celecoxib), or betamimetic agents (such as, for instance, Indacaterol, Formoterol, Levalbuterol), or anti-cholinergic agents (such as, for instance, Thiotropium, Glycopyrrolate, Ipratropium), or phosphodiesterase inhibitors (such as, for instance, Sildenafil, Vardenafil, Tadalafil), or endothelin antagonists (such as, for example, Bosentan, Sixtasentan, Tezosentan), or leukotriene antagonists (such as, for instance, Montelukast), or diuretics (such as, for instance, Furosemide, Amiloride), or immunomodulators (such as, for instance, Cyclosporin, Mofetil, Sirolimus, Tacrolimus), or antihypertensive agents (such as, for example, Statins, Sartans, calcium and angiotension antagonists), or mucolytics (such as, for instance, Dornase alpha, Bromhexine, Ambroxol, Acetylcysteine), or antibiotics of a variety of classes such as chinolons, macrolides, cephalosporins, aminogylcosides, ketolides, peptides and proteins, or interferons, or immunoglobulins, or prostins, or antimycotics, or antiviral agents, or heparin and heparinoids, or cytostatics, or endogenous substances which, owing to a gene defect such as, for instance, mucoviscidosis, or to illness, are not available in sufficient amounts in the body, such as, for instance, alpha-antitrypsin, interferons, insulin, or a combination of the above substances.

21. Method according to claim 20, wherein the administration strategy comprises a first phase, in which the aerosol generating device is operated with a first output rate, and a second phase, in which the aerosol generating device is operated with a second output rate, the first output rate being greater than the second output rate.

22. Method according to claim 21, wherein the first output rate is designed for the greatest possible deposition of aerosol in the lungs and the second output rate is designed to optimise utilisation of an active substance.

23. Method according to claim 21, wherein the first and second output rates can be applied and combined as desired in order to optimise an administration strategy.

24. Method of administering a substance, preferably a medicament, using an inhalation therapy device according to claim 1, wherein an administration strategy is used.

25. Inhalation therapy device comprising:

an aerosol generating device having a membrane for nebulising a fluid and providing liquid droplets; and a nebulising chamber having a respiratory air supply inlet, the air supply inlet having a center line and being configured to receive a flow of respiratory air from a ventilator, and a connecting piece configured for direct connection to a patient line at an outlet of the nebulising chamber, wherein the liquid droplets and the respiratory air are supplied to and mix in the nebulizing chamber to form a liquid droplet/respiratory air mixture that flows through the outlet, wherein the aerosol generating device is fixed substantially on the center line of the air supply inlet of the nebulising chamber, and wherein the air supply inlet is disposed to direct the flow of respiratory air onto a rear side of the aerosol generating device.

26. Inhalation therapy device according to claim 25, wherein the aerosol generating device, the outlet of the nebulising chamber and the respiratory air supply inlet of the nebulising chamber for supply of the respiratory air flow are aligned substantially along one axis and wherein the liquid droplets are provided only in a direction of the respiratory air flow.

27. Inhalation therapy device according to claim 25, wherein the nebulising chamber has a rotationally symmetrical configuration with an axis of rotation, wherein the respiratory air supply inlet is located on the axis of rotation, and wherein the aerosol generating device is fixed in the nebulising chamber on the axis of rotation.

28. Inhalation therapy device according to claim 25, wherein the membrane is positioned substantially on the center line of the outlet of the nebulising chamber.

29. Inhalation therapy device according to claim 25, wherein a center line of the outlet is aligned substantially to the center line of the air supply inlet.

* * * * *